(12) United States Patent
Han et al.

(10) Patent No.: US 6,955,904 B2
(45) Date of Patent: Oct. 18, 2005

(54) GENE CODING FOR QUINONE OXIDOREDUCTASE OF KLUYVEROMYCES MARXIANUS AND PROTEIN EXPRESSED THEREFROM

(75) Inventors: Ye Sun Han, Seoul (KR); Hun Yeoung Koh, Seongnam-si (KR); Hyewhon Rhim, Seoul (KR); Joo Hwan Cha, Seoul (KR); Wook Hyun Kim, Seoul (KR); Jung Ho Back, Jeonju-si (KR)

(73) Assignee: Korea Institute of Science and Technology, Seoul (KR)

( * ) Notice: Subject to any disclaimer, the term of this patent is extended or adjusted under 35 U.S.C. 154(b) by 235 days.

(21) Appl. No.: 10/306,651

(22) Filed: Nov. 26, 2002

(65) Prior Publication Data

US 2003/0175886 A1 Sep. 18, 2003

(30) Foreign Application Priority Data

Nov. 29, 2001 (KR) ......................................... 2001-74837

(51) Int. Cl.⁷ ............................ C12N 9/02; C12N 1/20; C12N 15/00; C12P 21/04; C07H 21/04
(52) U.S. Cl. ................. 435/189; 435/252.3; 435/320.1; 435/252.33; 435/4; 435/6; 435/69.7; 435/71.1; 536/23.2; 536/23.74
(58) Field of Search .............................. 435/189, 252.3, 435/320.1, 252.33, 69.1, 71.1, 4, 6, 252.8; 536/23.2, 23.74

*Primary Examiner*—Manjunath Rao
*Assistant Examiner*—Yong Pak
(74) *Attorney, Agent, or Firm*—Jones Day

(57) ABSTRACT

The invention is a gene coding for a quinone oxidoreductase from *Kluyveromyces marxianus* and a protein having an amino acid sequence expressed therefrom, which can be advantageously used in a reduction reaction of a quinone compound and synthesis of intermediates for a biologically active compound.

6 Claims, 10 Drawing Sheets

```
agtaatgtat ggcccaaaaa agggtaagta gtgttactat tgtcatcact gttaaaaatg    60
cgaatgaggg gaaagaaagt acatagttgc gtagccgatt ggttgttata gttgctgta    120
ttagtaagta agattgtaac taggagaaca gtacaattgc tacattttc aattgggttt    180
tcgatactct tctaagtgcc tgtcttgagc agtatagtat atactaagga ttttagctgt    240
gttgtattta actggcagga cgtttctgat ccacaaggaa tagattggct gtattgagag    300
gttagtttga cgtattgctg ctaattgcta ttttattatt ctattttatt cattgtaaag    360
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atg | tca | tca | ttc | cta | tca | aag | agg | ttc | att | tca | acc | aca | caa | aga | gca | 408  |
| Met | Ser | Ser | Phe | Leu | Ser | Lys | Arg | Phe | Ile | Ser | Thr | Thr | Gln | Arg | Ala |      |
| 1   |     |     |     | 5   |     |     |     |     | 10  |     |     |     |     | 15  |     |      |
| atg | tcc | caa | cta | cct | aaa | gcg | aag | tca | ttg | att | tat | tca | agc | cac | gac | 456  |
| Met | Ser | Gln | Leu | Pro | Lys | Ala | Lys | Ser | Leu | Ile | Tyr | Ser | Ser | His | Asp |      |
|     |     |     | 20  |     |     |     |     | 25  |     |     |     |     | 30  |     |     |      |
| cag | gat | gtg | tcc | aaa | att | ttg | aag | gtg | cat | acc | tat | caa | cca | aaa | ggc | 504  |
| Gln | Asp | Val | Ser | Lys | Ile | Leu | Lys | Val | His | Thr | Tyr | Gln | Pro | Lys | Gly |      |
|     |     | 35  |     |     |     |     | 40  |     |     |     |     | 45  |     |     |     |      |
| agt | gcg | gaa | tct | tct | att | ttg | ttg | aaa | acc | cta | gct | ttc | cca | att | aac | 552  |
| Ser | Ala | Glu | Ser | Ser | Ile | Leu | Leu | Lys | Thr | Leu | Ala | Phe | Pro | Ile | Asn |      |
| 50  |     |     |     |     | 55  |     |     |     |     | 60  |     |     |     |     |     |      |
| cct | tcg | gac | atc | aac | caa | tta | gaa | ggt | gtg | tat | cct | tcg | aag | ccg | gag | 600  |
| Pro | Ser | Asp | Ile | Asn | Gln | Leu | Glu | Gly | Val | Tyr | Pro | Ser | Lys | Pro | Glu |      |
| 65  |     |     |     |     | 70  |     |     |     |     | 75  |     |     |     |     | 80  |      |
| aag | gtg | ttg | gac | tac | tct | act | gaa | aag | cca | tct | gct | att | gct | ggt | aac | 648  |
| Lys | Val | Leu | Asp | Tyr | Ser | Thr | Glu | Lys | Pro | Ser | Ala | Ile | Ala | Gly | Asn |      |
|     |     |     |     | 85  |     |     |     |     | 90  |     |     |     |     | 95  |     |      |
| aaa | ggt | ttg | ttt | gag | gtt | gtt | tca | ttg | cca | tct | ggt | gtc | aaa | aac | ttg | 696  |
| Lys | Gly | Leu | Phe | Glu | Val | Val | Ser | Leu | Pro | Ser | Gly | Val | Lys | Asn | Leu |      |
|     |     |     | 100 |     |     |     |     | 105 |     |     |     |     | 110 |     |     |      |
| aag | gca | gga | gac | agg | gtc | atc | cca | ttg | cag | gcc | aac | ttt | ggt | aca | tgg | 744  |
| Lys | Ala | Gly | Asp | Arg | Val | Ile | Pro | Leu | Gln | Ala | Asn | Phe | Gly | Thr | Trp |      |
|     | 115 |     |     |     |     | 120 |     |     |     |     | 125 |     |     |     |     |      |
| tct | aca | tac | aga | act | tgc | gaa | agt | gaa | aac | gat | ctt | att | aag | ata | gaa | 792  |
| Ser | Thr | Tyr | Arg | Thr | Cys | Glu | Ser | Glu | Asn | Asp | Leu | Ile | Lys | Ile | Glu |      |
|     | 130 |     |     |     |     | 135 |     |     |     |     | 140 |     |     |     |     |      |
| ggt | gtg | gac | ttg | tat | act | gcc | gcc | aca | att | gct | gtt | aac | ggt | tgt | acg | 840  |
| Gly | Val | Asp | Leu | Tyr | Thr | Ala | Ala | Thr | Ile | Ala | Val | Asn | Gly | Cys | Thr |      |
| 145 |     |     |     |     | 150 |     |     |     |     | 155 |     |     |     |     | 160 |      |

Fig. 2a

```
gcc tac cag atg gtg aat gac tac att gag tgg gac cca tct ggt aat      888
Ala Tyr Gln Met Val Asn Asp Tyr Ile Glu Trp Asp Pro Ser Gly Asn
            165                 170                 175 gac tgg tta gtt caa aac gct ggt aca tca tca gtg tcc aag att gtt      936
Asp Trp Leu Val Gln Asn Ala Gly Thr Ser Ser Val Ser Lys Ile Val
            180                 185                 190 act caa atc gcc aag gac aaa ggc att aaa aca ttg agt gtt gtg aga      984
Thr Gln Ile Ala Lys Asp Lys Gly Ile Lys Thr Leu Ser Val Val Arg
            195                 200                 205 gat cgt gat aac ttt gat gaa gtc gca gag aac cta gag aag aag tat     1032
Asp Arg Asp Asn Phe Asp Glu Val Ala Glu Asn Leu Glu Lys Lys Tyr
            210                 215                 220 ggt gct act aag gtg att tcc gaa tct caa aac ggt gaa agg gag ttc     1080
Gly Ala Thr Lys Val Ile Ser Glu Ser Gln Asn Gly Glu Arg Glu Phe
225                 230                 235                 240 ggc aat gag gtc tta cca aag atc ttg gga cca aac gcc cag gtc aag     1128
Gly Asn Glu Val Leu Pro Lys Ile Leu Gly Pro Asn Ala Gln Val Lys
            245                 250                 255 ttg gcg ttg aac tct gtc ggt ggt aag tcg tgc act aac att gcc cgt     1176
Leu Ala Leu Asn Ser Val Gly Gly Lys Ser Cys Thr Asn Ile Ala Arg
            260                 265                 270 aag ttg tcc cct aac ggt ttg atg ttg act tac gga ggt atg tcc aaa     1224
Lys Leu Ser Pro Asn Gly Leu Met Leu Thr Tyr Gly Gly Met Ser Lys
            275                 280                 285 cag cca gtt act ctt cca acc ggg ttg ttt atc ttc aac agt ata aga     1272
Gln Pro Val Thr Leu Pro Thr Gly Leu Phe Ile Phe Asn Ser Ile Arg
            290                 295                 300 tcc cac ggt ttc tgg gtc act gct aac tcc aag aga gac cct gaa aat     1320
Ser His Gly Phe Trp Val Thr Ala Asn Ser Lys Arg Asp Pro Glu Asn
305                 310                 315                 320 aag aga aag act gtg gac gct gtt gtg aag tta tac cgc gat ggt          1365
Lys Arg Lys Thr Val Asp Ala Val Val Lys Leu Tyr Arg Asp Gly (SEQ ID NO:2)
            325                 330                 335 aaaccacaac actcacgaac cattcacttt attacagtta gttaactgca acttatggct   1425
aaacaaatat atgtatgtat gtatacttac atatataagt atatgaactt gaaacattca   1485
acaggacata ttctgccacg gtaaaggttg atgcagcttt taagtcagga ttctgaagat   1545
ccaatcgatg tttatgtgac tgcagctaga tgcgtacagg aactctccat acttacatac   1605
tttgctagat ttacttttca gcatgagtaa catgcggaat ttcggttgac atcgaaaaag   1665
gactccgtgg ccaagctggt taa (SEQ ID NO:1)                              1688
```

Fig. 2b

28S RNA
18S RNA

5S RNA

M    1

Michaelis-Menten plot
Effect of 1,4-benzoquinone concentration

Lineweaver-Burk plot
Effect of 1,4-benzoquinone concentration

GENE CODING FOR QUINONE OXIDOREDUCTASE OF KLUYVEROMYCES MARXIANUS AND PROTEIN EXPRESSED THEREFROM

FIELD OF THE INVENTION

The present invention relates to a gene coding for a quinone oxidoreductase from *Kluyveromyces marxianus* and a protein having an amino acid sequence expressed from the gene. More particularly, the present invention is directed to a gene coding for a quinone oxidoreductase having an amino acid sequence of SEQ. ID. NO: 2 and the quinone oxidoreductase expressed from the sequence.

BACKGROUND OF THE INVENTION

Products made by reduction of quinone compounds using reductases are known to produce reactive oxygen radicals. Reactive oxygen radicals are known to cause oxidative stress, damage DNA and cell membranes, and induce cancer. However, reductases such as quinone oxidoreductase prevent the formation of such free radicals (Anil K. Kaisuwal et al., Biochemical Pharmacology, 60 (2000), 207–214).

SUMMARY OF THE INVENTION

The object of this invention is to disclose the identy of a gene coding for a quinone oxidoreductase produced from microorganisms and to provide the quinone oxidoreductase by overexpressing the gene in a host cell.

Specifically, the present invention provides a gene coding for a quinone oxidoreductase having an amino acid sequence of SEQ. ID. NO: 2 and a quinone oxidoreductase expressed therefrom.

The gene is isolated from *Kluyveromyces marxianus* and encodes for an amino acid sequence for oxidoreductase of SEQ. ID. NO: 2. Also encompassed by the present invention are recombinant vectors containing the gene coding for *Kluyveromyces marxianus* quinone oxidoreductase and a suitable host, such as a bactetria, transformed with such recombinant vectors.

The invention is also for a process for preparing *Kluyveromyces marxianus* quinone oxidoreductase, comprising, culturing a suitable host, inducing expression of the quinone oxidoreductase by adding an expression inducer to the culture, and recovering and purifying the expressed quinone oxidoreductase.

BRIEF DESCRIPTION OF DRAWING

FIGS. 2a and 2b show a gene sequence (SEQ ID NO:1) and corresponding amino acid sequence (SEQ ID NO:2) for *Kluyveromyces marxianus* quinone oxidoreductase (kmQOR).

DETAILED DESCRIPTION OF THE PRESENT INVENTION

This disclosure is based on investigation to achieve the objects of the present invention which found that a quinone oxidoreductase is expressed in *Kluyveromyces marxianus*. The invention was completed by isolating and purifying the quinone oxidoreductase from *Kluyveromyces marxianus* and then determining the base sequence of the gene.

The present invention is, therefore, directed to the gene encoding the quinone oxidoreductase of *Kluyveromyces marxianus* and the protein having an amino acid sequence expressed from the isolated gene. The gene coding for *Kluyveromyces marxianus* quinone oxidoreductase codes a protein having the amino acid sequence of SEQ. ID. NO: 2 and a *Kluyveromyces marxianus* quinone oxidoreductase expressed therefrom.

The quinone oxidoreductase is obtained by first cloning the quinone oxidoreductase gene from *Kluyveromyces marxianus* to determine the base sequence of the gene. The gene is then expressed to produce a thermostable quinone oxidoreductase.

Figure 1:
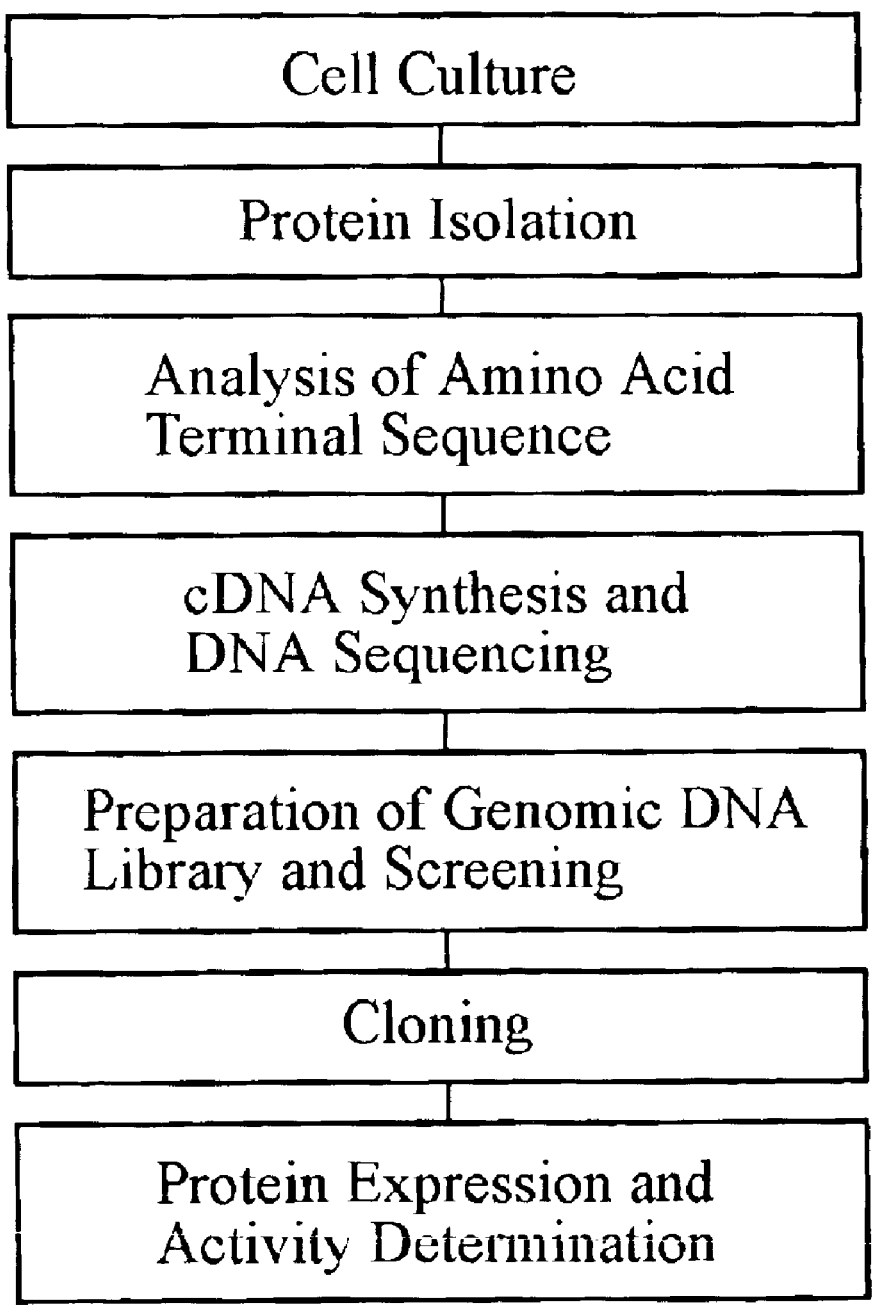
FIG. 1 is a flow chart for a gene cloning used in the present invention.

The flow chart in FIG. 1 was established to obtain the gene coding for quinone oxidoreductase. The strain of *Kluyveromyces marxianus* (KCTC 7155) used in the present invention was obtained from Daewoong Pharmaceutical Co., Ltd. (Seoul, Korea). After the microorganism is cultured, the cells are collected by cetrifugation and the obtained cells are lysed. The obtained cell extracts are isolated by centrifugation and the supernatant is separated by chromatography. Activity of each eluent of a substrate is determined by UV spectrophotometry. The eluents showing the activity are separated and purified. The purified proteins are subjected to electrophoresis on a SDS-polyacrylamide gel (PAGE) to identify the protein band.

The identified protein is transferred to a PVDF (Polyvinylidene Fluoride) membrane to indentify the terminal sequence of the protein, and the 5' primer for synthesizing cDNA is synthesized from the amino acid sequence.

Then, *Kluyveromyces marxianus* strain is cultured and collected by centrifugation to extract whole RNA. To facilitate the synthesis of cDNA, mRNA is purified from the whole RNA and then reverse transcriptase-polymerase chain reaction (RT-PCR) is carried out using the above synthesized 5' primers to synthesize cDNA from the purified mRNA. A polymerase chain reaction (PCR) is carried out using the synthesized cDNA and the obtained synthesized product is cloned in a cloning vector to determine the DNA sequence. The gene base sequence of the clone is determined by a chain termination method, and then the BLAST (Basic Local Alignment Search Tool) program is used to identify a quinone oxidoreductase showing the sequence similarity to the conventional reductases [Foster, C. E., Bianchet, M. A., Talalay, P., Zhao, Q., and Amzel, M. L., Biochemistry, 38 (1999), 9881–9886].

To obtain the gene to produce the quinone oxidoreductase, a plasmid library of *Kluyveromyces marxianus* is constructed as set forth below.

A genomic DNA of *Kluyveromyces marxianus* is purified, cut with different restriction enzymes and subject to southern blot hybridization to prepare an approximate gene map. Based on this, the plasmid library is prepared by using the restriction enzymes (EcoRI, XhoI), which cut the genomic DNA into fragments having an appropriate size.

To obtain a full length of a quinone oxidoreductase gene from the prepared library, colony hybridization screening is carried out using the probe (hereinafter, "QORp") (SEQ. ID. NO: 8) treated with the isotope ($^{32}$P). Base sequences of the clones that show a positive signal are determined by the dideoxynucleotide chain termination method.

To obtain the quinone oxidoreductase protein, the clones containing the quinone oxidoreductase gene are subjected to PCR with two synthetic oligonucleotides. The product is separated on agarose gel and the gene fragment of 1,143 bp is obtained. The fragment is treated with the restriction enzymes NdeI and XhoI and then ligated into NdeI/XhoI digested pET22b vector (Novagen Inc., Madison, Wis., USA) to prepare plasmid pQOR22b.

The synthetic oligonucleotides used, are designed to include restriction sites of the restriction enzymes used and to be accurately ligated to the translation start site. The synthetic oligonucleotides sequences are as follows:

```
kmQOR-F (SEQ. ID. NO: 3):
5'-TCATTGTACATATGTCATCATTCCTATCAAAG-3' kmQOR-R (SEQ. ID. NO: 4):
5'-GGTCTCGAGCCATTTCAACACAACCATATT-3'
```

The plasmid pQOR22b is transformed into an expression host cell, *E. coli* BL21 (DE3) [hsdS gal (λcI ts857 ind1 sam7 nin5 lacUV5-T7 gene1)] (Novagen Inc., Madison, Wis., USA) and grown on a medium. Thereafter, IPTG (β-D-isopropyl-D-thiogalactopyranoside) is added to the medium to induce the expression of the quinone oxidoreductase protein. After shaking culture, the cells are centrifuged and lysed. The obtained cell extracts are separated by means of chromatography, etc., and subjected to electrophoresis to identify the protein band.

An *E. coli* strain (*E. coli* BL21(DE3)/pET22b) containing pQOR22b was deposited under the Budapest Treaty in the Korean Collection for Type Cultures, located in #52, Oundong, Yusong-ku, Taejon 305–333. Republic of Korea, on Nov. 12, 2001 and assigned accession No. KCTC 10114 BP.

Activity of the quinone oxidoreductase on a substrate is determined by a UV spectrophotometer (UV-1601PC, SHIMADZU). The determination of the activity is performed by determining a change of optical density by oxidation of NADPH ($\epsilon_{340\ nm}$=6.23 mM$^{-1}$) at a wavelength of 340 nm with the concentration of 1,4-benzoquinone changed. To obtain more accurate results, several experiments are carried out and an average of the determined values can be calculated to obtain a rate constant for the reaction. As described in detail in the following examples, it has been found that the *Kluyveromyces marxianus* quinone oxidoreductase of the present invention shows a very high activity to reduce a quinone compound.

The present invention is further described with the following examples which should not be construed as limiting the invention.

EXAMPLE 1

Isolation and Purification of Quinone Oxidoreductase from *Kluyveromyces Marxianus*

Figure 3:
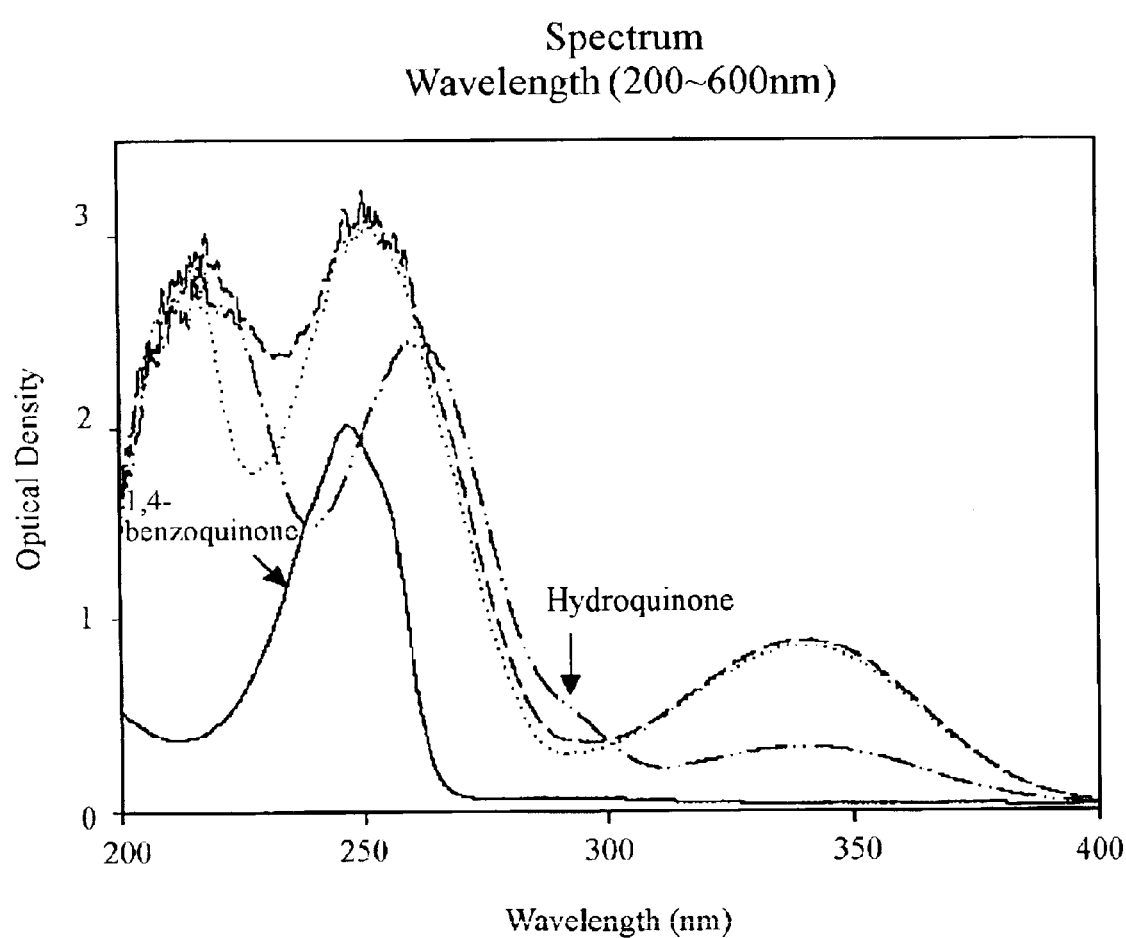
FIG. 3 shows a spectrum detecting activity of the quinone oxidoreductase using a UV spectrophotometer.

A strain of *Kluyveromyces marxianus* (KCTC 7155) screened by Daewoong Pharmaceutical Co., Ltd. (Seoul, Korea) was grown on 8.0 liter of YM medium for 72 hours at 30° C. until $OD_{600}$ becomes 7.0. The cultured cells were collected by centrifugation for 10 minutes at 3,000 G and dissolved in 200 ml of a diluent solution (50 ml Na phosphate, pH 6.5, 1 mM phenylmethylsulfonyl fluoride (PMSF)). Thereafter, French Press cell was operated under a pressure of 11,000 bar to lyse the cells and the cells were further lysed by operating a sonicator (Branson sonifier, Model 450) 5 times for 5 minutes per operation. The obtained cell extracts were centrifuged for 30 minutes at 25,000 G and the supernatant was separated by a cation exchange chromatography (S-sepharose, Pharmacia). Then, activity of each eluent on a substrate was determined by a UV spectrophotometer (UV-1601PC, SHIMADZU) (FIG. 3).

Ammonium sulfate (AMS) was added to the collected eluents showing the activity to make the AMS concentration 1.2M and the solution was subjected to sequential treatment of phenyl-sepharose, HiTrap-Blue sepharose (affinity column) chromatography and gel filtration chromatography (Superdex-75, Pharmacia). The purified proteins were subjected to electrophoresis on a 12% SDS-polyacrylamide gel (PAGE) and, as a result, proteins with a size of 42 kDa were identified.

Figure 4:
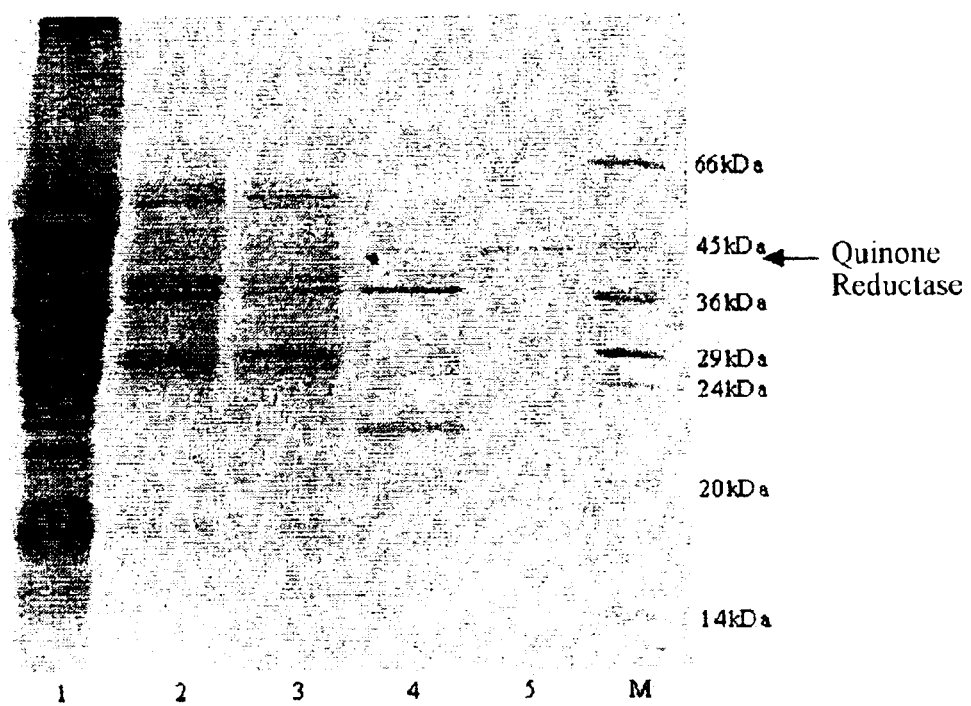
FIG. 4 is an autoradiogram showing the results of electrophoresis on an SDS-polyacrylamide gel (12%) of the quinone oxidoreductase protein for identificating purification of the protein.

In FIG. 4, lane 1 is a supernatant of the lysed cells, lanes 2, 3, 4 and 5 are fractions separated from S-sepharose, phenyl-sepharose, HiTrap-Blue sepharose and Superdex-75 chromatography, respectively, and M is a standard-sized sample.

The identified protein was transfered to PVDF membrane to indentify the terminal amino acid sequence of the protein and 5' primers 1 and 2 for synthesizing cDNA were synthesized from the amino acid sequence.

```
Primer 1 (SEQ. ID. NO: 5):
5'-ATGTCYTCNTTNCTNTCNAANAG-3'

Primer 2 (SEQ. ID. NO: 6):
5'-ATGTCYTCYTTDCTDTCYAAYAG-3'
```

Figure 5A:
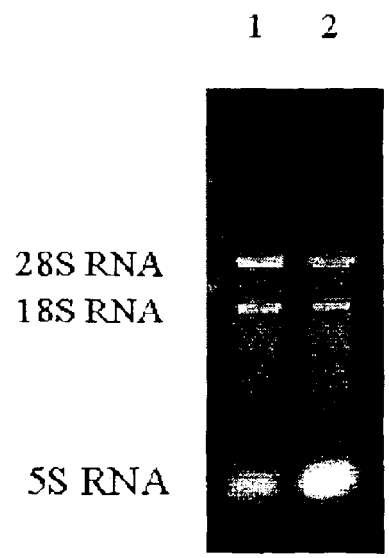
FIG. 5a is an autoradiogram showing total RNA which is purified from *Kluyveromyces marxianus*.

EXAMPLE 2 cDNA Synthesis of *Kluyveromyces marxianus* Quinone Oxidoreductase and DNA Sequence Determination The strain of *Kluyveromyces marxianus* was cultured on 100 ml YM medium for 72 hours at 30° C. and the cultured cells were collected by cetrifugation at 3,000 G. Using TRIZOL solution (GIBCO BRL, Life Technologies), the whole RNA was extracted from the microorganisms (FIG. 5a). FIG. 5a is an autoradiogram showing the electrophoresis result of the whole RNA, which was extracted from *Kluyveromyces marxianus*, on 1.2% formaldehyde agarose gel. In FIG. 5a, lanes 1 and 2 show the whole RNA of *Kluyveromyces marxianus*.

Figure 5B:
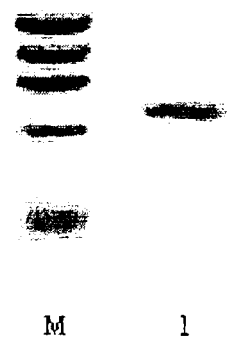
FIG. 5b is an autoradiogram showing the results obtained by polymerase chain reaction of cDNA that is prepared from the RNA purified from *Kluyveromyces marxianus*.

To facilitate the synthesis of cDNA, mRNA was purified from the whole RNA. Reverse transcriptase-polymerase chain reaction (RT-PCR; 30° C. 10 minute, 42° C. 30 minute, 96° C. 5 minute, 1 cycle) was carried out using the primers synthesized in Example 1 to synthesize cDNA from the purified mRNA. The synthesized cDNA was subjected to PCR (primers 1 and 2, M13 primer M4 (SEQ. ID. NO. 7), 94° C. 30 second, 48° C. 30 second, 72° C. 30 second, 5 cycles, 94° C. 30 second, 50° C. 30 second, 72° C. 30 second, 30 cycles) (FIG. 5b). In FIG. 5b, lane 1 is a HaeIII marker and lane 2 is a reation product of primer 1 and M13 primer M4.

To determine the DNA sequence, the obtained products were cloned to TA cloning vector. The base sequences of 18 clones were determined by a chain termination method, and then the sequences were analyzed with BLAST (Basic Local Alignment Search Tool) program. As a result, a quinone oxidoreductase showing a sequence similarity to the conventional reductases was identified.

The clone having the sequence similarity to conventional reductases had a size of about 639 bp (SEQ. ID. NO: 8) and was used as a probe (QORp) for searching a full length of a quinone oxidoreductase gene.

EXAMPLE 3

Cloning Quinone Oxidoreductase Gene

To obtain a gene expressing a quinone oxidoreductase, the flow chart for gene cloning as shown in FIG. 1 was established. First, a plasmid library was prepared from *Kluyveromyces marxianus* as described below.

A genomic DNA of *Kluyveromyces marxianus* was purified, cut with 10 different restriction enzymes and identified by southern blotting hybridization to prepare an approximate restriction enzyme map. Based on this, the plasmid library was prepared by using the restriction enzymes (EcoRI, XhoI) which cut the genomic DNA into fragments having an appropriate size.

The prepared library was screened by colony hybridization. The screening was carried out using the probe (QORp) treated with the isotope ($^{32}$P). In primary screening, 4 clones that showed a positive signal were obtained and in secondary screening, more than 20 clones showed a strongly positive signal. Among 20 clones, 10 clones were selected and southern blotting hybridization was carried out. As a result, it was again confirmed that the target gene was present. Base sequence of one clone was determined by the dideoxynucleotide chain termination method (FIG. 2).

EXAMPLE 4

Expression and Purification of Quinone Oxidoreductase

After examining the restriction enzyme map and the base sequence, the gene coding for the quinone oxidoreductase was expressed in *E. coli* to obtain the quinone oxidoreductase protein.

First, an expression vector, pET22b (Novagen, Inc.) to the C-terminal of which 6 histidine amino acid-encoding nucleotides can be bound, was linearized by cutting with NdeI/XhoI. The clones containing the quinone oxidoreductase gene were subjected to PCR with two synthetic oligonucleotides and then the product was separated on agarose gel to obtain the gene fragement having a size of 1,143 bp. The frafment was treated with the restriction enzymes NdeI and XhoI and then ligated into the NdeI/XhoI digested pET22b vector to prepare a plasmid pQOR22b.

The above noted synthetic oligonucleotides were designed to include restriction sites for the restriction enzymes utilized and to be accurately ligated to the translation start site. The synthetic oligonucleotides sequences were as follows:

```
kmQOR-F (SEQ. ID. NO: 3):
5'-TCATTGTACATATGTCATCATTCCTATCAAAG-3' kmQOR-R (SEQ. ID. NO: 4):
5'-GGTCTCGAGCCATTTCAACACAACCATATT-3'
```

Figure 6:
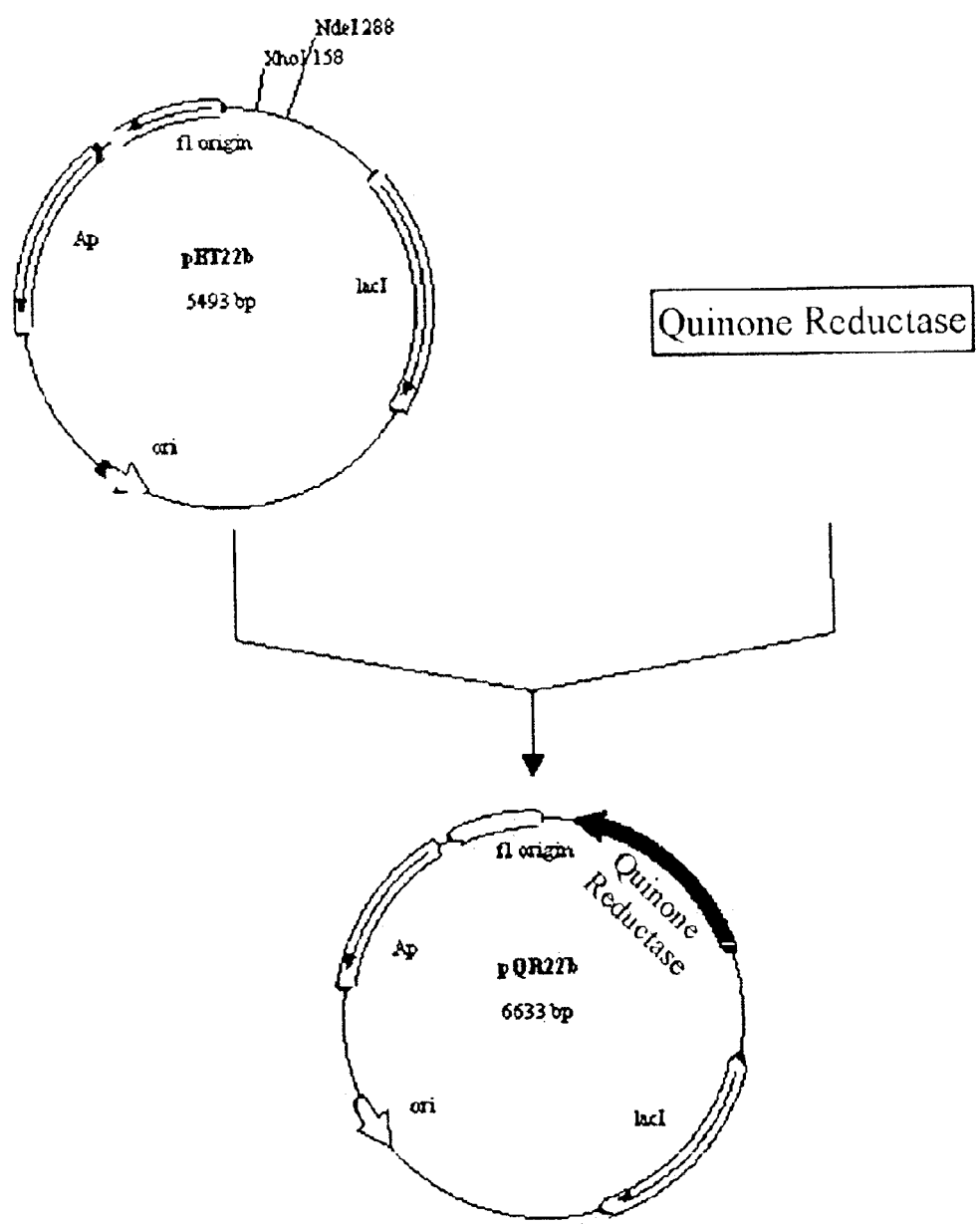
FIG. 6 illustrates the preparation of vector pQOR22b for overexpressing *Kluyveromyces marxianus* quinone oxidoreductase.

The plasmid pQOR22b was transformed into a expression host cell, *E. coli* BL21 (DE3) [hsdS gal (λcI ts857 ind1 sam7 nin5 lacUV5-T7 gene1) Novagen Inc., FIG. 6].

*E. coli* BL21 (DE3), transformed with the quinone oxidoreductase gene, was inoculated in 1 liter of LB medium containing 100 μg/μl of ampicillin and grown at 37° C. until $OD_{600}$ becomes 0.6. Production of the *Kluyveromyces marxianus* quinone oxidoreductase protein was then induced by the addition of IPTG to the medium at a final concentration of 500 μM.

After incubation with shaking for 4 hours, the cells were harvested by centrifugation for 10 min at 3,000 G. The obtained cells were resolved in 25 ml of dilution solution (20 mM Tris-HCl, pH7.9, 500 mM NaCl, 5 mM imidazole, 1 mM PMSF) and lysed by operating a sonicator (Branson sonifier, Model 450) 3 times for 5 minutes per operation. The obtained cell extracts were centrifuged for 30 minutes at 25,000 G and the supernatant was separated by a HiTrap Chelating column (Pharmacia) and then gel filtration chromatography (Superdex-75, Pharmacia). The purified proteins were subjected to electrophoresis on a 12% SDS-polyacrylamide gel and, as a result, a band of protein having a size of approximate 42 kDa was identified (FIGS. 7a and 7b).

Figure 7A:
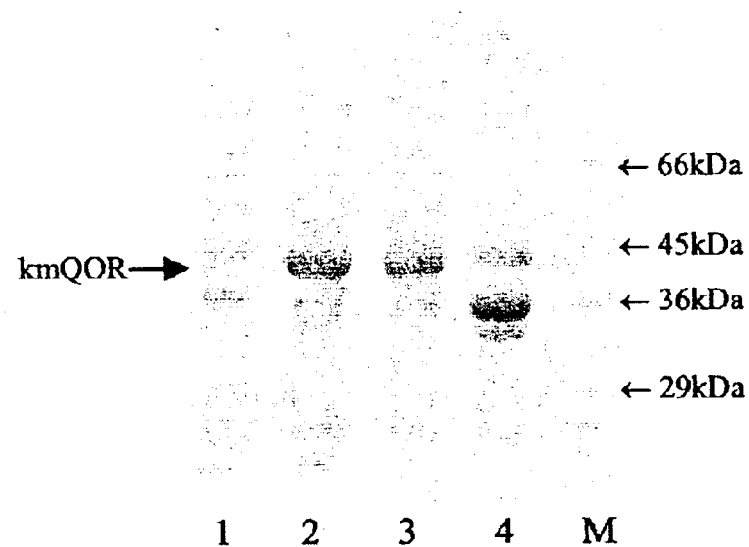
FIG. 7a is an autoradiogram showing the results of electrophoresis on an SDS-polyacrylamide gel (12%) for identificating overexpression of the quinone oxidoreductase protein in *E coli*.

FIG. 7a shows the results of electrophoresis on an SDS-polyacrylamide gel (12%), lane 1 is a crude extract of uninduced cells, lane 2 is a crude extract of induced cells that were incubated for 4 hours after IPTG was added, lane 3 is a soluble fraction after centrifugation of the cells that were incubated for 4 hours after IPTG was added, lane 4 is a centrifuged pellet of the cells that were incubated for 4 hours after IPTG was added, and M is a standard-sized sample.

Figure 7B:
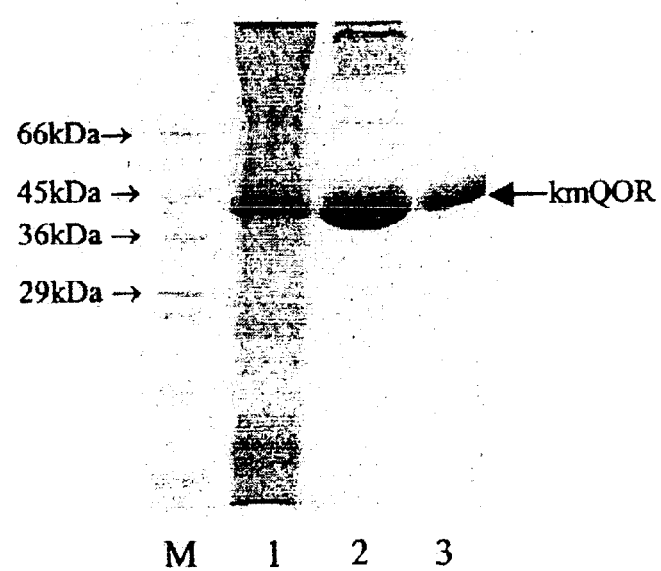
FIG. 7b is an autoradiogram showing the results of electrophoresis on an SDS-polyacrylamide gel (12%) for identificating purification of the quinone oxidoreductase protein in *E coli*.

FIG. 7b shows the result of electrophoresis on an SDS-polyacrylamide gel (12%), M is a standard-sized sample, lane 1 is a soluble fraction of the lysed cells, lane 2 and 3 are fractions separated from HiTrap Chelating sepharose and Superdex-75 chromatography, respectively.

EXAMPLE 5

Determination of Activity of Quinone Oxidoreductase

Activity of the present quinone oxidoreductase on a substrate was performed by using a UV spectrophotometer (UV-1601PC, SHIMADZU). The reduction reaction was performed in a 1 ml reaction mixture containing 2 μM quinone oxidoreductase, 50 mM Na phosphate buffer solution, pH 6.5, and 1,4-benzoquinone. The reduction reaction was initiated immediately after 200 μM NADPH was added to the reaction solution at 25° C.

Figure 8A:
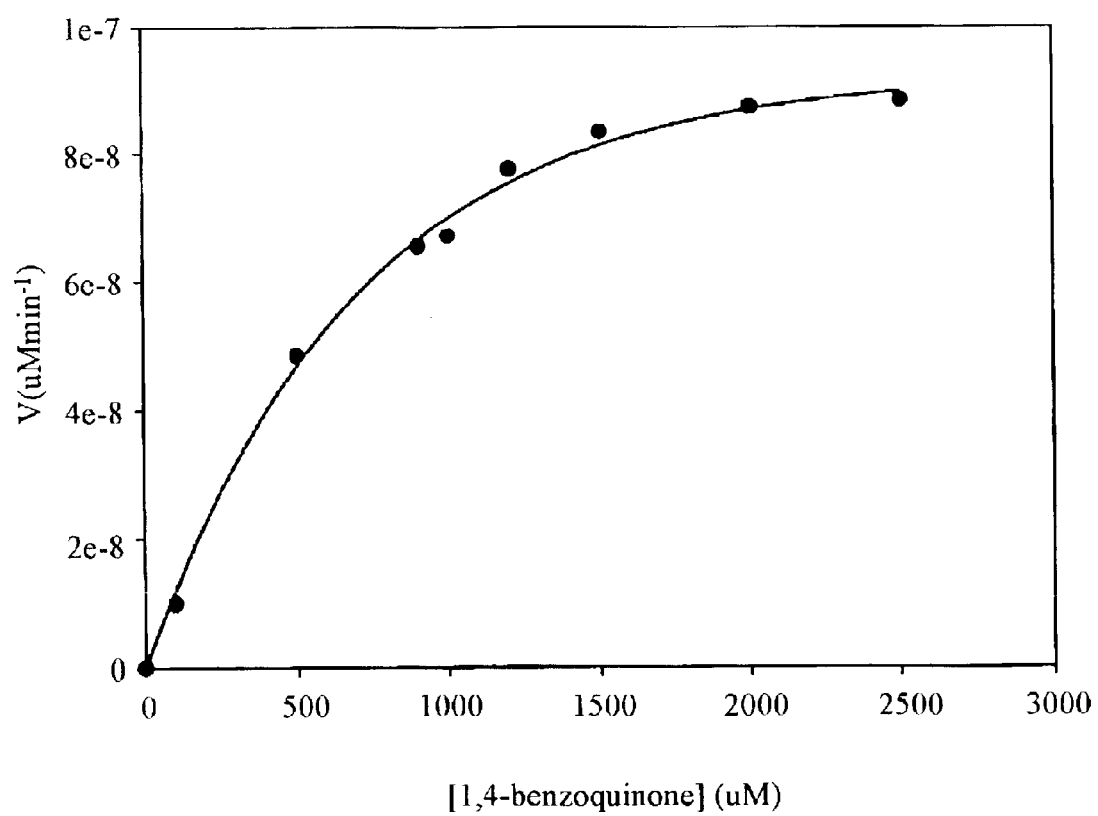
FIG. 8 is a graph showing activity of the purified quinone oxidoreductase.
Figure 8B:
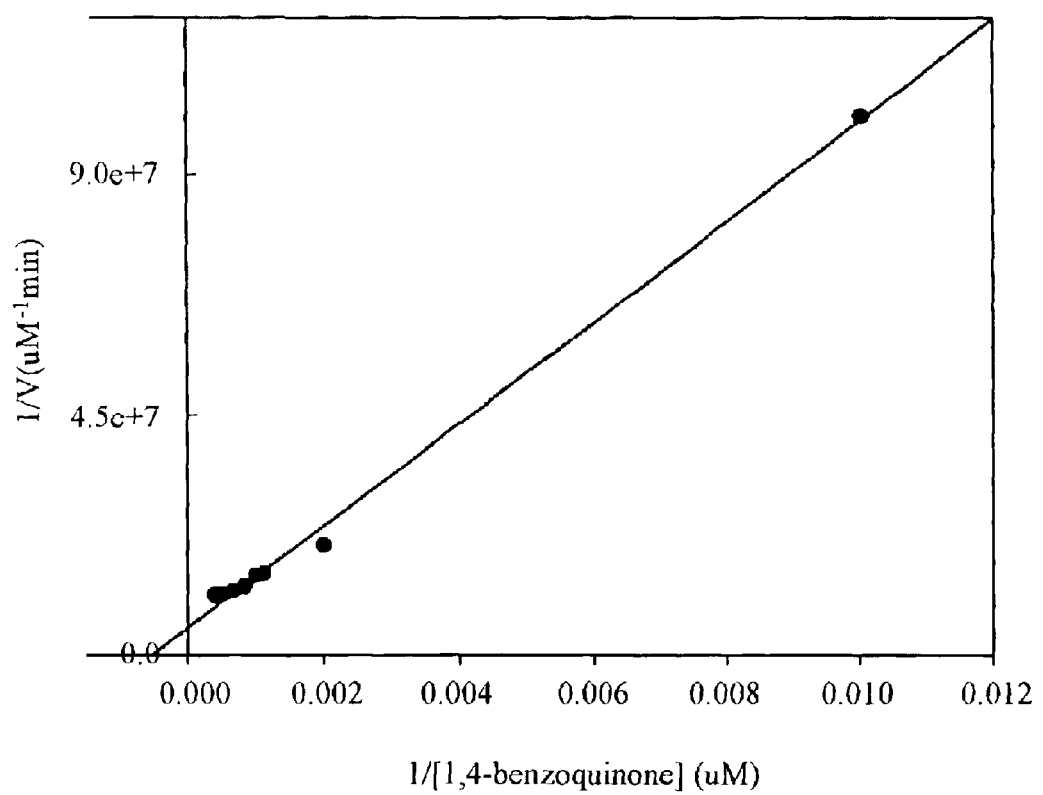

The determination of the activity was performed by determining a change of optical density by oxidation of NADPH ($\epsilon_{340\ nm}$=6.23 $mM^{-1}$) at a wavelength of 340 nm with the concentration of 1,4-benzoquinone changed from 10 μM to 200 μM. To obtain more accurate results, the experiments were carried out three times and an average of the determined values was calculated to obtain a rate constant for the reaction. The rate constant for the reaction of the quinone oxidoreductase on 1,4-benzoquinone (kcat/Km) was $5.3 \times 10^7$ $M^{-1}m^{-1}$ (Km=1.8 mM, kcat=$9.5 \times 10^5$ $m^{-1}$) (FIG. 8).

The activity of other quinone oxidoreductases is described for reference. A rate constant for the reaction of human quinone oxidoreductase on α-tocopherol quinone is $1.5 \times 10^7$ $M^{-1}m^{-1}$ (Siegel, D., Bolton, E. M., Burr, J. A. Leibler, D. C., and Ross, D. Mol. Pharmacol. 37 (1997) 300–305). A rate constant for the reaction of Arabidopsis thaliana quinone oxidoreductases on duroquinone is $3.2 \times 10^7$ $M^{-1}m^{-1}$ (Sparla, F., Tedeschi, G., Pupillo, P., Trost, P. FEBS Letters 463 (1999) 382–386).

As seen above, *Kluyveromyces marxianus* quinone oxidoreductase of the present invention has a superior ability to reduce a quinone compound so that it can be advantageously used in a reduction reaction of a quinone compound and synthesis of intermediate of a biologically active compound.

---

What is claimed is:

1. An isolated polynucleotide encoding a *Kluyveromyces marxianus* quinone oxidoreductase having the amino acid sequence of SEQ. ID. NO:2.

2. A recombinant vector comprising the polynucleotide of claim 1.

3. The recombinant vector of claim 2, which is plasmid pQOR22b.

4. An *E. coli* transformed with the recombinant vector of claim 2.

5. The *E. coli* of claim 4, which is BL21(DE3)pET22b.

6. A process for producing a *Kluyveromyces marxianus* quinone oxidoreductase, comprising the steps of:
   culturing the *E. coli* of claim 4;
   inducing an expression of the quinone oxidoreductase by adding IPTG in culture; and
   recovering and purifying the expressed quinone oxidoreductase.

* * * * *

SEQUENCE LISTING

<160> NUMBER OF SEQ ID NOS: 8

<210> SEQ ID NO 1
<211> LENGTH: 1688
<212> TYPE: DNA
<213> ORGANISM: Kluyveromyces marxianus
<220> FEATURE:
<221> NAME/KEY: CDS
<222> LOCATION: (361)..(1365)

<400> SEQUENCE: 1

```
agtaatgtat ggcccaaaaa agggtaagta gtgttactat tgtcatcact gttaaaaatg    60
cgaatgaggg gaaagaaagt acatagttgc gtagccgatt ggttgttata gtttgctgta   120
ttagtaagta agattgtaac taggagaaca gtacaattgc tacatttttc aattgggttt   180
tcgatactct tctaagtgcc tgtcttgagc agtatagtat atactaagga tttttagctgt   240 gttgtattta actggcagga cgtttctgat ccacaaggaa tagattggct gtattgagag   300
gttagtttga cgtattgctg ctaattgcta ttttattatt ctattttatt cattgtaaag   360 atg tca tca ttc cta tca aag agg ttc att tca acc aca caa aga gca    408
Met Ser Ser Phe Leu Ser Lys Arg Phe Ile Ser Thr Thr Gln Arg Ala
1               5                  10                  15 atg tcc caa cta cct aaa gcg aag tca ttg att tat tca agc cac gac    456
Met Ser Gln Leu Pro Lys Ala Lys Ser Leu Ile Tyr Ser Ser His Asp
             20                  25                  30 cag gat gtg tcc aaa att ttg aag gtg cat acc tat caa cca aaa ggc    504
Gln Asp Val Ser Lys Ile Leu Lys Val His Thr Tyr Gln Pro Lys Gly
         35                  40                  45 agt gcg gaa tct tct att ttg ttg aaa acc cta gct ttc cca att aac    552
Ser Ala Glu Ser Ser Ile Leu Leu Lys Thr Leu Ala Phe Pro Ile Asn
     50                  55                  60 cct tcg gac atc aac caa tta gaa ggt gtg tat cct tcg aag ccg gag    600
Pro Ser Asp Ile Asn Gln Leu Glu Gly Val Tyr Pro Ser Lys Pro Glu
65                  70                  75                  80 aag gtg ttg gac tac tct act gaa aag cca tct gct att gct ggt aac    648
Lys Val Leu Asp Tyr Ser Thr Glu Lys Pro Ser Ala Ile Ala Gly Asn
                 85                  90                  95 aaa ggt ttg ttt gag gtt gtt tca ttg cca tct ggt gtc aaa aac ttg    696
Lys Gly Leu Phe Glu Val Val Ser Leu Pro Ser Gly Val Lys Asn Leu
            100                 105                 110 aag gca gga gac agg gtc atc cca ttg cag gcc aac ttt ggt aca tgg    744
Lys Ala Gly Asp Arg Val Ile Pro Leu Gln Ala Asn Phe Gly Thr Trp
        115                 120                 125 tct aca tac aga act tgc gaa agt gaa aac gat ctt att aag ata gaa    792
Ser Thr Tyr Arg Thr Cys Glu Ser Glu Asn Asp Leu Ile Lys Ile Glu
    130                 135                 140 ggt gtg gac ttg tat act gcc gcc aca att gct gtt aac ggt tgt acg    840
Gly Val Asp Leu Tyr Thr Ala Ala Thr Ile Ala Val Asn Gly Cys Thr
```

-continued

| | | |
|---|---|---|
| gcc tac cag atg gtg aat gac tac att gag tgg gac cca tct ggt aat<br>Ala Tyr Gln Met Val Asn Asp Tyr Ile Glu Trp Asp Pro Ser Gly Asn<br>165                               170                        175 | 888 | |

```
gcc tac cag atg gtg aat gac tac att gag tgg gac cca tct ggt aat    888
Ala Tyr Gln Met Val Asn Asp Tyr Ile Glu Trp Asp Pro Ser Gly Asn
            165                 170                 175 gac tgg tta gtt caa aac gct ggt aca tca tca gtg tcc aag att gtt    936
Asp Trp Leu Val Gln Asn Ala Gly Thr Ser Ser Val Ser Lys Ile Val
                180                 185                 190 act caa atc gcc aag gac aaa ggc att aaa aca ttg agt gtt gtg aga    984
Thr Gln Ile Ala Lys Asp Lys Gly Ile Lys Thr Leu Ser Val Val Arg
        195                 200                 205 gat cgt gat aac ttt gat gaa gtc gca gag aac cta gag aag aag tat    1032
Asp Arg Asp Asn Phe Asp Glu Val Ala Glu Asn Leu Glu Lys Lys Tyr
    210                 215                 220 ggt gct act aag gtg att tcc gaa tct caa aac ggt gaa agg gag ttc    1080
Gly Ala Thr Lys Val Ile Ser Glu Ser Gln Asn Gly Glu Arg Glu Phe
225                 230                 235                 240 ggc aat gag gtc tta cca aag atc ttg gga cca aac gcc cag gtc aag    1128
Gly Asn Glu Val Leu Pro Lys Ile Leu Gly Pro Asn Ala Gln Val Lys
                245                 250                 255 ttg gcg ttg aac tct gtc ggt ggt aag tcg tgc act aac att gcc cgt    1176
Leu Ala Leu Asn Ser Val Gly Gly Lys Ser Cys Thr Asn Ile Ala Arg
            260                 265                 270 aag ttg tcc cct aac ggt ttg atg ttg act tac gga ggt atg tcc aaa    1224
Lys Leu Ser Pro Asn Gly Leu Met Leu Thr Tyr Gly Gly Met Ser Lys
        275                 280                 285 cag cca gtt act ctt cca acc ggg ttg ttt atc ttc aac agt ata aga    1272
Gln Pro Val Thr Leu Pro Thr Gly Leu Phe Ile Phe Asn Ser Ile Arg
    290                 295                 300 tcc cac ggt ttc tgg gtc act gct aac tcc aag aga gac cct gaa aat    1320
Ser His Gly Phe Trp Val Thr Ala Asn Ser Lys Arg Asp Pro Glu Asn
305                 310                 315                 320 aag aga aag act gtg gac gct gtt gtg aag tta tac cgc gat ggt        1365
Lys Arg Lys Thr Val Asp Ala Val Val Lys Leu Tyr Arg Asp Gly
                325                 330                 335 aaaccacaac actcacgaac cattcacttt attacagtta gttaactgca acttatggct    1425
aaacaaatat atgtatgtat gtatacttac atatataagt atatgaattt gaaacattca    1485
acaggacata ttctgccacg gtaaaggttg atgcagcttt taagtcagga ttctgaagat    1545
ccaatcgatg tttatgtgac tgcagctaga tgcgtacagg aactctccat acttacatac    1605
tttgctagat ttacttttca gcatgagtaa catgcggaat ttcggttgac atcgaaaaag    1665
gactccgtgg ccaagctggt taa                                            1688
```

<210> SEQ ID NO 2
<211> LENGTH: 335
<212> TYPE: PRT
<213> ORGANISM: Kluyveromyces marxianus

<400> SEQUENCE: 2

```
Met Ser Ser Phe Leu Ser Lys Arg Phe Ile Ser Thr Thr Gln Arg Ala
1               5                   10                  15

Met Ser Gln Leu Pro Lys Ala Lys Ser Leu Ile Tyr Ser Ser His Asp
                20                  25                  30

Gln Asp Val Ser Lys Ile Leu Lys Val His Thr Tyr Gln Pro Lys Gly
            35                  40                  45

Ser Ala Glu Ser Ser Ile Leu Leu Lys Thr Leu Ala Phe Pro Ile Asn
        50                  55                  60

Pro Ser Asp Ile Asn Gln Leu Glu Gly Val Tyr Pro Ser Lys Pro Glu
```

```
                65                  70                  75                  80
        Lys Val Leu Asp Tyr Ser Thr Glu Lys Pro Ser Ala Ile Ala Gly Asn
                            85                  90                  95

Lys Gly Leu Phe Glu Val Val Ser Leu Pro Ser Gly Val Lys Asn Leu
                           100                 105                 110

Lys Ala Gly Asp Arg Val Ile Pro Leu Gln Ala Asn Phe Gly Thr Trp
                           115                 120                 125

Ser Thr Tyr Arg Thr Cys Glu Ser Glu Asn Asp Leu Ile Lys Ile Glu
                   130                 135                 140

Gly Val Asp Leu Tyr Thr Ala Thr Ile Ala Val Asn Gly Cys Thr
        145                 150                 155                 160

Ala Tyr Gln Met Val Asn Asp Tyr Ile Glu Trp Asp Pro Ser Gly Asn
                           165                 170                 175

Asp Trp Leu Val Gln Asn Ala Gly Thr Ser Ser Val Ser Lys Ile Val
                           180                 185                 190

Thr Gln Ile Ala Lys Asp Lys Gly Ile Lys Thr Leu Ser Val Val Arg
                   195                 200                 205

Asp Arg Asp Asn Phe Asp Glu Val Ala Glu Asn Leu Glu Lys Lys Tyr
                   210                 215                 220

Gly Ala Thr Lys Val Ile Ser Glu Ser Gln Asn Gly Glu Arg Glu Phe
        225                 230                 235                 240

Gly Asn Glu Val Leu Pro Lys Ile Leu Gly Pro Asn Ala Gln Val Lys
                           245                 250                 255

Leu Ala Leu Asn Ser Val Gly Gly Lys Ser Cys Thr Asn Ile Ala Arg
                           260                 265                 270

Lys Leu Ser Pro Asn Gly Leu Met Leu Thr Tyr Gly Gly Met Ser Lys
                           275                 280                 285

Gln Pro Val Thr Leu Pro Thr Gly Leu Phe Ile Phe Asn Ser Ile Arg
                   290                 295                 300

Ser His Gly Phe Trp Val Thr Ala Asn Ser Lys Arg Asp Pro Glu Asn
        305                 310                 315                 320

Lys Arg Lys Thr Val Asp Ala Val Val Lys Leu Tyr Arg Asp Gly
                           325                 330                 335

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 3
tcattgtaca tatgtcatca ttcctatcaa ag                                    32

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 4
ggtctcgagc catttcaaca caaccatatt                                       30

<210> SEQ ID NO 5
<211> LENGTH: 23
<212> TYPE: DNA
<213> ORGANISM: Artificial Sequence
```

```
<220> FEATURE:
<223> OTHER INFORMATION: Description of Artificial Sequence: primer
<220> FEATURE:
<221> NAME/KEY: misc_feature
<222> LOCATION: (1)..(23)
<223> OTHER INFORMATION: n is 'a, t, c, or g'

<400> SEQUENCE: 5
atgtcytcnt tnctntcnaa nag                                              23

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 6
atgtcytcyt tcctdtcyaa yag                                              23

<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: M13 primer
       M4

<400> SEQUENCE: 7
gttttcccag tcacgac                                                     17

<210> SEQ ID NO 8
<211> LENGTH: 639
<212> TYPE: DNA
<213> ORGANISM: Kluyveromyces marxianus

<400> SEQUENCE: 8
atgtcatcat tcctatcaaa gaggttcatt tcaaccacac aaagagcaat gtcccaacta      60
cctaaagcga agtcattgat ttattcaagc cacgaccagg atgtgtccaa aattttgaag     120
gtgcatacct atcaaccaaa aggcagtgcg gaatcttcta ttttgttgaa aaccctagct     180
ttcccaatta acccttcgga catcaaccaa ttagaaggtg tgtatccttc gaagccggag     240
aaggtgttgg actactctac tgaaaagcca tctgctattg ctggtaacaa aggtttgttt     300
gaggttgttt cattgccatc tggtgtcaaa aacttgaagg caggagacag ggtcatccca     360
ttgcaggcca actttggtac atggtctaca tacagaactt gcgaaagtga aaacgatctt     420
attaagatag aaggtgtgga cttgtatact gccgccacaa ttgctgttaa cggttgtacg     480
gcctaccaga tggtgaatga ctacattgag tgggacccat ctggtaatga ctggttagtt     540
caaaacgctg gtacatcatc agtgtccaag attgttactc aaatcgccaa ggacaaaggc     600
attaaaacat tgagtgttgt gagagatcgt gataacttt                            639
```